United States Patent
Lefebvre et al.

(10) Patent No.: US 10,215,740 B2
(45) Date of Patent: Feb. 26, 2019

(54) METHOD FOR MANUFACTURING A GAS PHASE CHROMATOGRAPHY COLUMN AND COLUMN OBTAINED USING SUCH A METHOD

(71) Applicants: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); UNIVERSITE CLAUDE BERNARD LYON 1, Villeurbanne (FR); CPE LYON FCR, Villeurbanne (FR)

(72) Inventors: David Lefebvre, Biviers (FR); Bernadette Charleux, Lyons (FR); Florence Ricoul, Quaix-en-Chartreuse (FR); Chloe Thieuleux, Villeurbanne (FR)

(73) Assignees: Commissariat à l'énergie atomique et aux énergies alternatives, Paris (FR); CENTRE NATIONAL DE LA RECHERCHE SCIENTIFQUE, Paris (FR); UNIVERSITE Claude Bernard LYON 1, Villeurbanne (FR); CPE Lyon FCR, Villeurbanne (FR)

( * ) Notice: Subject to any disclaimer, the term of this patent is extended or adjusted under 35 U.S.C. 154(b) by 300 days.

(21) Appl. No.: 14/908,935

(22) PCT Filed: Jul. 28, 2014

(86) PCT No.: PCT/EP2014/066205
§ 371 (c)(1),
(2) Date: Jan. 29, 2016

(87) PCT Pub. No.: WO2015/014808
PCT Pub. Date: Feb. 5, 2015

(65) Prior Publication Data
US 2016/0169844 A1    Jun. 16, 2016

(30) Foreign Application Priority Data

Jul. 31, 2013 (FR) .................................. 13 57615

(51) Int. Cl.
*G01N 30/56* (2006.01)
*B05D 3/04* (2006.01)
(Continued)

(52) U.S. Cl.
CPC ............. *G01N 30/56* (2013.01); *B05D 3/044* (2013.01); *B05D 3/065* (2013.01); *B05D 7/227* (2013.01);
(Continued)

(58) Field of Classification Search
CPC ............. G01N 30/56; G01N 2030/486; G01N 2030/525; G01N 2030/528; G01N 2030/567
See application file for complete search history.

(56) References Cited

U.S. PATENT DOCUMENTS 7,595,350 B2 * 9/2009 Xu ..................... B01J 20/28042
                                                              210/656
2007/0172960 A1   7/2007 Malik et al.
(Continued)

FOREIGN PATENT DOCUMENTS

GB        1 045 349 A    10/1966
WO        00/11463 A1     3/2000

OTHER PUBLICATIONS

Wen Li, et al., "Sol-gel stationary phases for capillary electrochromatography," Journal of Chromatography A, vol. 1044, No. 1-2, XP004522960, Jul. 30, 2004 (pp. 23-52).
(Continued)

*Primary Examiner* — Robert Clemente
(74) *Attorney, Agent, or Firm* — Oblon, McClelland, Maier & Neustadt, L.L.P.

(57) ABSTRACT

The present invention relates to a method for manufacturing a chromatography column, in particular for a gas phase (Continued)

chromatography, comprising a stationary phase made from a sol.

This method comprises the following steps:

(a) introducing this sol at the first end of the column, (b) moving said sol towards the second end of the column, so that a sol layer is formed on the internal wall of the column, this layer being able to form a gel on said internal wall, and (c) drying of the gel.

The present invention also relates to a capillary column as well as to a microcolumn which may be manufactured according to this method.

33 Claims, 2 Drawing Sheets

(51) Int. Cl.
 *B05D 3/06* (2006.01)
 *B05D 7/22* (2006.01)
 *G01N 30/02* (2006.01)

(52) U.S. Cl.
 CPC . *G01N 2030/025* (2013.01); *G01N 2030/567* (2013.01)

(56) References Cited

U.S. PATENT DOCUMENTS

2011/0132196 A1\* 6/2011 Suzuki .................. B01D 53/02
 96/105
2014/0060331 A1\* 3/2014 Peene ................ G01N 30/6078
 96/101

OTHER PUBLICATIONS

Zhenghua Ji, et al., "Porous layer open-tubular capillary columns: preparations, applications and future directions," Journal of Chromatography A, vol. 842, No. 1-2, XP004167268, May 21, 1999 (pp. 115-142).

J. Vial, et al., "Silica sputtering as a novel collective stationary phase deposition for microelectromechanical system gas chromatography column: Feasibility and first separations," Journal of Chromatography A, vol. 1218, 2011 (pp. 3262-3266).

J. Rouquerol, et al., "Recommendations for the Characterization of Porous Solids," Pure & Applied Chemistry, vol. 66, No. 8, 1994 (pp. 1739-1758).

International Search Report dated Oct. 7, 2014 in PCT/EP2014/066205 filed Jul. 28, 2014.

French Search Report dated Apr. 2, 2014 in FR 1357615 filed Jul. 31, 2013.

U.S. Appl. No. 14/389,051, filed Sep. 29, 2014, US2015/0068280 A1, Florence Ricoul.

U.S. Appl. No. 14/438,711, filed Apr. 27, 2015, US2015/0251127 A1, Florence Ricoul, et al.

\* cited by examiner

METHOD FOR MANUFACTURING A GAS PHASE CHROMATOGRAPHY COLUMN AND COLUMN OBTAINED USING SUCH A METHOD

CROSS-REFERENCE TO RELATED APPLICATIONS

This application is a U.S. national-stage filing of PCT/EP2014/066205, filed Jul. 28, 2014 which claims priority to France 1357615, filed Jul. 31, 2015.

TECHNICAL FIELD

The present invention relates to a method for manufacturing a chromatography column, in particular in a gas phase, comprising a stationary phase, this stationary phase being made from a sol. The invention more particularly relates to a method for manufacturing a capillary column or a microcolumn.

The present invention also relates to a capillary column as well as to a microcolumn which may be manufactured by such a method.

STATE OF THE PRIOR ART

Gas chromatography or GC as an acronym, like all chromatographic techniques, is a technique which allows separation and analysis of molecules present in a mixture. This technique mainly applies to molecules formed by gas compounds or which may be vaporized by heating without being broken down.

To do this, the gas mixture is introduced into a column which contains a stationary phase and is then transported through the column by means of a gas, a so-called carrier gas. The different molecules of the mixture separate within the column and flow out of this column one after the other, after a time lapse which is function of the affinity of these molecules with the stationary phase.

From among the columns most commonly used in gas chromatography, capillary columns are known, formed by a hollow capillary tube, the internal diameter of which is less than 2 mm, advantageously less than 1 mm.

Recently, microcolumns have been developed, the latter being made in solid substrates by applying micro-manufacturing techniques, in particular micro-machining or photolithography. A microcolumn thus comprises a microtrench formed, for example by etching, in a wafer such as a silicon wafer. The inner wall of the microtrench is coated with a porous stationary phase which may be deposited by spraying for example. The microcolumn further comprises a hood sealed on the wafer intended to close the microtrench, and to delimit a channel through which flows the mixture to be analyzed. This hood may be formed by another wafer or by a layer which may notably be in silicon, in silicon oxide or in a polymeric material.

The capillary columns, or the microcolumns, generally have an internal diameter, or at least one of the internal transverse lengths, of less than 1 mm, most often comprised between 20 μm and 500 μm. Their lengths may be comprised between a few tens of cm and 100 m.

Certain capillary columns designated by the term PLOT, an acronym of Porous Layer Open Tubular, include a solid and porous stationary phase with a thickness conventionally comprised between 5 nm and 50 μm.

These PLOT capillary columns comprise an organic or inorganic stationary phase which has a large developed surface allowing them to retain lightweight molecules by interactions of the gas/solid type. These columns are mainly used for separating permanent gases and organic compounds appearing in gaseous form at room temperature, the permanent gases being defined as gases for which the critical temperature is less than room temperature and which may not be liquefied by simple compression. These are for example hydrogen, oxygen, nitrogen, argon, hydrogen sulfide or further methane. Among the organic compounds appearing in gaseous form at room temperature, mention may notably be made of lightweight hydrocarbons, such as linear or branched alkanes fitting the formula $C_nH_{2n+2}$, n being an integer less than or equal to 5, alkenes or further dienes such as pentadiene.

The inorganic stationary phases commonly used in PLOT capillary columns are stationary phases in porous silica, in porous alumina or in a porous polymer. Such inorganic stationary phases in silica or in alumina actually resist quite well to the so-called "bleeding" phenomenon. This "bleeding" phenomenon is expressed by detachment of portions of stationary phase occurring when chromatographic analysis is conducted at a high temperature. These stationary phase portions which have been detached are transferred into the gas flow formed by the carrier gas and the vaporized mixture, which reduces the efficiency of the capillary column. Further, these stationary phase portions will increase the base line of the chromatogram and thereby contribute to the signal detected at the output of the chromatography column, when certain types of detectors, such as a flame ionization detector (FID acronym), are used.

A stationary phase in porous silica may however be preferred to a stationary phase in porous alumina for separating organic compounds appearing in gaseous form at room temperature and which are reactive like pentadiene, since such organic compounds may be degraded by the catalytic activity of the alumina.

However, the present methods applied for the manufacturing of porous capillary columns do not give the possibility of forming capillary columns with a small diameter, in particular for which the diameter is less than 250 μm.

Now, it is well established that capillary gas chromatography columns with a circular section are all the more efficient in terms of separation of the molecules present in the mixture since their internal diameter is small. In particular, the smaller the internal diameter, the more specific and rapid is the chromatographic separation. A contrario, the smaller the internal diameter, the more the total capacity of the column decreases, the more the volume of the stationary phase decreases.

Also, the object of the invention is to propose a method giving the possibility of filling this gap, by giving the possibility of forming capillary columns of the PLOT type, for which the diameter may attain a few tens of μm, while controlling the characteristics of the stationary phase thereof, and in particular the thickness and/or the porosity, over the whole length of the column.

Moreover, the invention also applies to the microcolumns mentioned earlier. It notably gives the possibility of making microcolumns with a small section for example having at least one of its transverse internal lengths measuring a few tens of μm, the stationary phase of which is porous.

Microcolumns of the PLOT type have already been described, notably in the publication (J. Vial et al., *Journal of Chromatography A*, 1218, 2011, pages 3262-3266, [1]).

In this publication [1], the authors achieve the deposition, on the internal wall of a microtrench made in a silicon wafer, of a stationary phase of porous silicon by ion spraying. They obtain the deposit, in a microtrench with a depth of 100 µm and a width of 75 µm, of a silica stationary phase having a thickness of the order of 0.75 µm, which allows them to successfully separate a mixture comprising methane, ethane, propane and butane. However, as the porosity of this deposited stationary phase is not sufficiently significant, the authors have, in a first phase, increased its thickness up to a value of the order of 1.5 µm. Next, in a second phase, they developed a chip with pillars for ensuring total separation of methane and ethane expressed by distinct peaks on the baseline. Now, both of these strategies are accompanied with certain drawbacks: a stationary phase with a too large thickness decreases the efficiency of the separation, and the use of a chip with pillars imposes resorting to large operating pressures, which does not always allow the use of the microcolumn at its optimum operating point. Further, this method should be accomplished before setting into place and sealing the hood on the silicon wafer, which does not give the possibility of having a homogeneous deposit of porous silica stationary phase over the whole internal wall of the microcolumn.

The object of the invention is therefore to overcome the drawbacks of the prior art and to propose a method for manufacturing a chromatography column, in particular for gas phase chromatography, comprising a stationary phase which may be applied for a capillary column as well as for a microcolumn of small dimensions, i.e. for a capillary column having an internal diameter of less than or equal to 2 mm, advantageously less than or equal to 1 mm, preferably comprised between 50 µm and 500 µm and, still more preferentially, between 50 µm and 250 µm, as well as for a microcolumn for which at least one of the internal transverse lengths is less than or equal to 500 µm, advantageously less than or equal to 250 µm and, preferably, comprised between 20 nm and 250 nm.

This method should further give the possibility of obtaining a stationary phase which is regularly and homogenously deposited on the whole of the internal wall of the chromatography column. In particular, when this column is a microcolumn, the stationary phase should also be present on the internal wall of the microtrench and of the hood forming this microcolumn.

DISCLOSURE OF THE INVENTION

The objects mentioned earlier as well as other ones are achieved, firstly, by a method for manufacturing a chromatography column, in particular for gas phase chromatography, of the capillary column or microcolumn type, comprising a stationary phase, this stationary phase being made from a sol (or a sol-gel solution), the method comprising the following steps:
(a) introducing this sol at a first end of the column,
(b) moving said sol towards the second end of the column, so that a sol layer is formed on the internal wall of the column, this layer being able to form a gel on said internal wall, and
(c) drying of the gel.

Such a method may advantageously be applied to capillary columns or to microcolumns of small dimensions.

According to an embodiment, the sol comprises a pore-forming agent and the method further comprises the following step (d):
(d) removing the pore-forming agent from the formed layer, so as to form a porous layer, and in particular a microporous or mesoporous layer, the size and/or the density of the pores being controlled, this porous layer forming the stationary phase.

The method according to the invention may also include one or several of the following features, taken individually or according to the technically feasible combinations:
prior to introducing the sol into the column, the internal wall of the column is subject to a so called "preparation" treatment, able to reinforce the adhesion of the sol on the internal wall, such a treatment aiming at increasing the hydrophilicity of the wall;
prior to introducing the sol into the column, the internal wall of the column is subject to a so-called "activation" treatment able to reinforce the adhesion of the stationary phase, such a treatment aiming at allowing covalent grafting between the gel and the internal wall during the condensation of the gel;
the sol forms a plug, extending from the first end of the column and over a length of less than two thirds, preferably less than half, advantageously less than the third and, preferentially less than the tenth of the total length of the column, the plug being moved along the column under the effect of pressure, in particular under the effect of pressure of a gas or of a supercritical fluid;
the pore-forming agent is selected from a surfactant, in particular from cetyltrimethylammonium bromide (CTAB), diblock copolymers of ethylene oxide and of propylene oxide, and triblock copolymers of ethylene oxide and of propylene oxide;
the pore-forming agent is a poly(ethylene oxide) with an average molar mass comprised between 50,000 and 300,000 g/mol or a polyethyleneglycol with an average molar mass comprised between 50,000 and 300,000 g/mol. By average molar mass is meant a number or mass average molar mass;
the step (d) for removing the pore-forming agent is achieved at the end of the drying step (c), by a treatment selected from calcination, washing, for example by means of an organic solvent of the alcohol or acetone type, and UV insolation preferentially in a redox medium;
the gas applied in step (b) and/or in step (c) is an inert gas such as helium or nitrogen, or air, in particular dry air.

The sol-gel technique is well known to one skilled in the art. Generally, the sol-gel solution or "sol" includes one or several precursors based on metal or metalloid elements (organometal compounds or metal salts), one or several solvents (for example, an organic solvent) and, preferably, a pore-forming agent.

The precursors contained in this sol undergo a hydrolysis step and a condensation step, in order to form a network of oxides confining the solvent, so as to form a gel.

The gel is then dried, in order to form a solid material.

Thus, the sol includes a precursor material, generally selected from compounds of formula $M(X)_n$, wherein:
X is a hydrolyzable group, preferentially selected from alkoxy, esters and halogens groups, preferably alkoxy (in particular methoxy or preferably ethoxy) groups, and
M represents silicon (n=4), aluminium (n=3) or a tetravalent metal (n=4), for example Ti, Zr or even Sn.

The sol also includes a solvent, in particular an organic solvent, and water, and preferably a hydrolysis catalyst.

Preferably, the precursor material is a silane, in particular tetraethyl orthosilicate, also designated as tetraethoxysilane or TEOS as an acronym, which gives the possibility of producing a stationary phase in silica.

The applied reactions are schematically written as:

  Hydrolysis reaction:

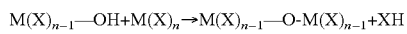

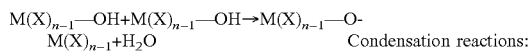  Condensation reactions:

These reactions, first of all, lead to the formation of a solution which is called a "sol", but which may be, depending on the conditions under which is carried out the hydrolysis of the oxide precursors, either a sol in the strict sense (i.e. a solution containing chemical species as colloids), or a solution containing chemical species as oligomers or polymers, and then to the formation of a "gel" (i.e. an elastic viscous mass having a set liquid structure) which consists of a mineral polymeric network and for which the viscosity increases over time.

Resorting to a stationary phase of the sol-gel type, and in particular to a stationary phase based on silica, allows good retention of lightweight gas species, such as hydrocarbons having 5 carbon atoms or less, or of permanent gases, while having a good resistance at high temperature (i.e. of the order of 250° C.). At the present time, it is not possible to obtain such performances by applying a stationary phase of the polymer type.

Thus, an object of the invention is a chromatography column, in particular for gas phase chromatography, including a stationary phase assuming the form of a porous layer, notably in silica, which may have a thickness of less than or equal to 1 μm and which may have a diameter of the pores of the layer preferentially comprised between 1 and 10 nm.

After removing the solvent phase confined in the gel, this gel may be subject to additional treatments like, for example, a heat treatment allowing it to be densified.

By forming the stationary phase directly in the column, it is possible to benefit from the condensation reactions of silanes for grafting, with covalent bonds, the stationary phase on the substrate, which is formed in this case by the internal wall of the column.

The term of "directly" designates the fact that the stationary phase is formed in the column, by hydrolysis and condensation, after having been deposited on this column. Thus, the stationary phase is not formed prior to the deposition, but afterwards. Aggregation and clogging problems of the column are then avoided during the deposition.

Further, it is estimated that this imparts better adhesion of the stationary phase.

Further, it is understood that such a method is adapted to any shape of the section of the column, whether it is circular or polygonal.

Thus, the grafting of the stationary phase on the internal wall of the column ensures greater stability of this stationary phase, in particular when chromatographic analyses are conducted at a high temperature. The phenomenon of "bleeding" or detachment of stationary phase pieces in the gas flow formed by the carrier gas and the vaporized mixture no longer occurs with columns manufactured according to the method of the invention.

Further, resorting to a sol-gel method applying pore-forming agents gives the possibility of obtaining a porous stationary phase, in particular a mesoporous phase, for which the porosity is under control. The distribution of the pores is then controlled, these pores may be distributed regularly, according to a controlled network and pore density.

In the foregoing and in the following, by "mesoporous stationary phase", is meant a porous stationary phase for which the size of the pores is comprised between 2 and 50 nm, according to the recommendations for the characterization of porous solids of the International Union of Pure Applied Chemistry (Rouqudrol et al., *Pure & Applied Chemistry*, 66(8), 1994, pages 1739-1758, [2]).

It will be noted that the method according to the invention also gives the possibility of obtaining a microporous stationary phase, i.e. a stationary phase for which the size of the pores is less than 2 nm, according to the recommendations of IUPAC ([2]). Generally, the size of the pores may vary between 1 nm and 10 nm. The size of the pores depends on the nature of the pore-forming agent used.

The gas chromatography column may be a capillary column, in which case it has a circular section which has an internal diameter of less than or equal to 2 mm, advantageously less than or equal to 1 mm, preferably comprised between 50 μm and 500 μm, and more preferentially between 50 μm and 250 μm.

This gas chromatography column may also be a microcolumn as defined above and for which at least one of the internal transverse lengths is less than or equal to 500 μm, advantageously less than or equal to 250 μm, and preferably comprised between 20 nm and 250 nm.

In an advantageous version of the invention, the internal wall of the column, before application of the method, is in silicon, in silica, in molten silica, in polymer or in metal. There is no particular restriction as regards the general material of the column, and of its internal wall in particular.

The particularity of this sol-gel deposition is to form the stationary phase directly inside the column, by a so called dynamic coating method.

The term of "dynamic" designates the fact that the sol is introduced through one first end of the column, and then moved along this column, as far as a second end, so that a thin sol layer is formed on the internal wall, notably because of the hydrophilicity of the internal wall. According to a preferred embodiment, the introduced solution appears as a plug, which is gradually moved from the first end to the second end, for example under the effect of pressure exerted by a gas or by a supercritical fluid such as supercritical $CO_2$.

It was observed that the thickness of the thereby formed stationary phase is less than 500 nm, this measurement being carried out by observing a section with a scanning electron microscope, after drying and removing the pore-forming agent.

According to one embodiment, these deposition and then drying steps may be repeated. In other words, the method may be repeated one or several times, so as to form a stationary phase with greater thickness, for example up to 1 or 3 μm, or even beyond.

The characteristics of the stationary phase, such as its thickness, its porosity may easily be modified by acting on different parameters of the method, such as the dilution of the sol, its deposition rate or further the amount of sol introduced into the first end of the column, the key parameters being the speed and the dilution. These parameters are determined experimentally.

In an advantageous alternative of the invention, the formed stationary phase has a thickness of less than or equal to 3 μm, advantageously comprised between 50 nm and 1 μm, and preferentially between 200 and 500 nm.

According to one embodiment of the invention, step (a) is carried out by dipping the first end of the column into the sol contained in a flask and by applying pressure of a gas or of a supercritical fluid inside the flask.

The gas or the supercritical fluid used during step (a) may be the same one as the one applied during step (b).

This gas may notably be air but also an inert gas such as helium or nitrogen.

According to another advantageous alternative of the invention, step (c) is carried out with circulation of gas inside the column.

This gas may be the same as the one applied during step (b) and, if necessary, during step (a).

According to a first alternative of the invention, step (d) is carried out by calcination.

This calcination may be carried out by circulating a dry gas inside the column, the temperature of this gas being advantageously comprised between 100° C. and 500° C.

A dry gas which may be oxygen or further an inert gas such as helium or nitrogen is advantageously used.

According to one second alternative of the invention, step (d) is carried out by washing with a solvent, this solvent advantageously being an alcohol or a ketone.

According to another alternative of the invention, reproducing steps (a) to (c) at least once before applying step (d) may be contemplated.

According to one particularly advantageous alternative of the invention, the method further comprises a step for activating the internal wall of the column, this activation step being carried out before step (a).

Indeed, the grafting of the stationary phase on the internal wall of the column may be advantageously improved by activating this internal wall.

This step for activating the internal wall of the column may be carried out by oxidation of said internal wall.

In the case when this activation is carried out with oxidation, it gives the possibility of generating on this internal wall of the column, so called reactive bonds comprising oxygen atoms, such as Si—OH or A-OH bonds, A designating the substrate on which the —OH groups of the gel may be bound by a condensation reaction. Indeed, the more the internal wall of the column has reactive bonds on which groups are capable of generating a covalent bond, in particular oxo bridges, during condensation of the gel, better will be the grafting and, consequently, adhesion of the thereby formed stationary phase.

Such an activation may not be necessary when the internal wall of the column has bonds comprising oxygen atoms, for example when the internal wall of the column or the column itself is in silicon or in silica, since such silanol bonds already exist at such a wall. However, activation by oxidation of such an internal wall may advantageously give the possibility of increasing the density of the silane reactive groups and, consequently, the adhesion of the stationary phase on the internal wall of the column.

This activation step by oxidation of the internal wall of the column may be achieved with a plasma, via a gas route or, preferentially, via a liquid route.

According to an advantageous alternative of the invention, the method further comprises a step for preparing the internal wall of the column, this preparation step being carried out before step (a), in order to increase the hydrophilicity of the internal wall. It is understood that this promotes deposition of the sol-gel solution on the wall following the displacement of the solution inside the column. The goal is to obtain, preferably, a wetting angle (towards water) of less than 20°. This preparation step may coincide with the activation step described earlier, in particular when this activation step is an oxidizing treatment.

The invention secondly relates to a capillary column which may be manufactured with the method according to the invention, this capillary column having an internal diameter of less than or equal to 2 mm, advantageously less than or equal to 1 mm, preferably comprised between 50 μm and 500 μm, and more preferentially between 50 μm and 250 μm.

The invention thirdly relates to a microcolumn which may be manufactured with the method according to the invention, this microcolumn having at least one of its internal transverse lengths of less than or equal to 500 μm, advantageously less than or equal to 250 μm, and preferably comprised between 20 nm and 250 nm.

Other features and advantages of the invention will become better apparent upon reading the additional description which follows, which relates to an exemplary device which may be applied with the method for manufacturing a gas chromatography column according to the invention as well as to two chromatographic separations and analyses carried out from a mixture of n-alkanes, one with a capillary column, the other with a microcolumn.

Of course, the examples which follow are only given as an illustration of the object of the invention and by no means are a limitation of this object.

DETAILED DISCLOSURE OF THE INVENTION AND OF PARTICULAR EMBODIMENTS

Figure 1A:
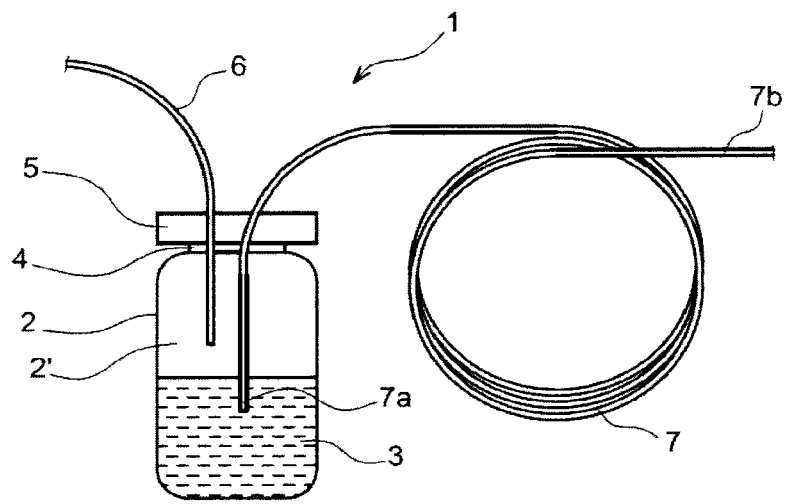
FIGS. 1A and 1B schematically illustrate a device allowing application of the method for manufacturing a chromatography column according to the invention, this column being a capillary column.

As illustrated in FIG. 1A, the device 1 giving the possibility of applying the method for manufacturing a chromatography column according to the invention, comprises a flask 2 which is partly filled with a sol 3.

The sol 3 is a colloidal suspension which comprises a solid phase with a grain size of less than 0.2 μm, dispersed in a liquid phase. The solid phase is prepared from the tetraethoxysilane (TEOS) precursor of formula $Si(OC_2H_5)_4$.

The liquid phase is an aqueous solution which comprises an alcohol (ethanol) and a surfactant.

The surfactant plays the role of a pore-forming agent since it allows formation in the sol of spherical micelles of the same size, these micelles delimiting spaces or pores. The surfactant therefore gives the possibility of obtaining a network of ordered mesopores and of controlling the developed surface of the obtained stationary phase. Indeed, by means of a surfactant, the porosity of the stationary phase is under control. The size and the distribution of the pores are controlled.

From among the surfactants which may be used in the sol, mention may be made of cationic surfactants such as cetyltrimethylammonium bromide (acronym CTAB) or amphiphilic diblock or triblock copolymers such as the triblock copolymer marketed by Aldrich under the trade name of Pluronic F127.

In an alternative of the invention, the surfactant is present in the sol in a surfactant/Si molar ratio comprised between 0.08 and 0.2, and advantageously of the order of 0.1. Such a surfactant/Si ratio gives the possibility of obtaining a three-dimensional pore-forming lattice, for example cubic or hexagonal. Indeed, with a surfactant/Si ratio being greater than 0.2, the pore-forming lattice is lamellar and has great likelihood of collapsing during the calcination step aiming at removing the surfactant.

This flask 2 is provided, at its neck 4, with a septum 5. This septum 5 is sealably crossed by a tube 6 for injecting a gas into the flask 2, on the one hand, and by a capillary column 7 intended to form a chromatography column according to the invention, on the other hand.

In the place of the capillary column 7, it would be quite possible to arrange a microcolumn.

Prior to putting a first end of the column in contact with the sol-gel solution, the internal wall of the column is subject to a treatment by oxidation, so as to increase the density of OH groups present at the surface. This has the consequences:
- the increase in the hydrophilicity of the internal wall, which promotes deposition of sol on the internal wall during sweeping of the column with the sol plug,
- the generation of sites for grafting the material forming the stationary phase with the internal wall.

This treatment by oxidation is carried out via a liquid route by having a solution formed with ethanol, water and soda pass through the inside of the column, followed by rinsing with deionized water and then drying.

The injection tube 6 is connected to a gas supply source (not shown) and opens into the upper portion 2' of the flask 2, above the level of the sol 3.

The gas is advantageously an inert gas, such as helium or nitrogen. But this gas may also be air. In this case, the humidity level of the air is controlled so as not to interfere with the conditions for applying the sol-gel deposition.

The applied gas pressure is adapted according to the dimensions of the capillary column 7. This applied gas pressure is advantageously less than or equal to 10 bars and, preferentially comprised between 0.2 and 4 bars. A gas pressure of the order of 2 bars is particularly preferred for a capillary column with a diameter of 100 μm and with a length of 2 m.

The capillary column 7, as for it, plunges into the sol 3 at its first end 7a, its second end 7b, located outside the flask 2, being left at atmospheric pressure.

Although there is no limitation as to its both transverse and longitudinal dimensions, the capillary column 7 has an internal diameter which is less than or equal to 2 mm, advantageously less than or equal to 1 mm. Preferably, this internal diameter is comprised between 50 μm and 500 μm and, still more preferentially, between 50 μm and 250 μm. It also has a length which is advantageously comprised between 10 cm and 100 m, advantageously between 50 cm and 50 m and, still more preferentially, between 1 m and 30 m.

This device 1, in its configuration illustrated in FIG. 1A, gives the possibility of carrying out the step for sampling a determined amount of sol 3. To do this, gas is injected through the injection tube 6 into the inside of the flask 2. Under the effect of the overpressure generated by the injection of gas into the flask 2, the sol 3 is pushed into the internal cavity of the capillary column 7.

Figure 1B:
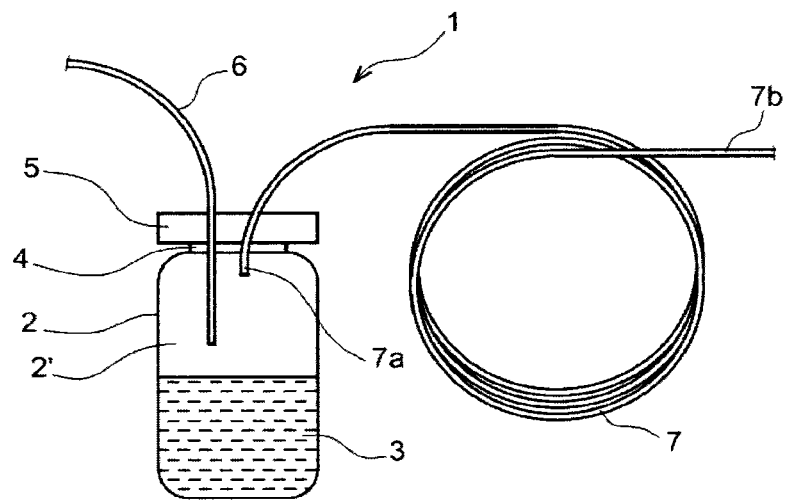

When the introduced amount of sol 3 is sufficient, for example when the sol forms a plug with a length comprised between 20 and 50 cm inside the column, the capillary column 7 is then slightly pulled in order to position it so that its first end 7a opens into the upper portion 2' of the flask 2 and no longer plunges into the sol 3. This configuration of the device 1 is illustrated in FIG. 1B.

This step which has just been described gives the possibility of forming a "plug" of sol in the cavity of the capillary column 7, from its first end 7a. The amount of plug sampled from the sol 3 is very clearly greater than the required amount for coating the whole internal wall of the capillary column 7, as this will be seen hereafter.

Under the effect of maintaining the overpressure inside the flask 2, this plug is then pushed into the internal cavity of the capillary column 7. During the gradual displacement of the plug inside and along the capillary column 7, a thin sol layer is deposited on the internal wall of this capillary column 7. Consequently, the plug loses a portion of its volume gradually during this displacement of the plug inside and along the capillary column 7. However, the initially sampled amount of sol is adapted so that this loss is negligible. This thin sol layer adheres to this internal wall because of its hydrophilicity related to the presence, in the sol, of silane groups which will form covalent bonds with this internal wall.

The thickness of this thin sol layer deposited on the internal wall of the capillary column 7 may be adjusted by the concentration of solvent in the sol. The higher this concentration, the more the thickness of this thin sol layer decreases during the drying step which will be described below. The thickness of this thin sol layer may also be adjusted by the displacement speed of the plug of sol inside and along the capillary column 7. This displacement speed of the plug of sol as for it depends on the overpressure of applied gas but also on the amount of sampled sol plug and on the viscosity of the sol, the latter parameter in turn depending on the composition of the sol.

When the sol plug has attained the second end 7b of the capillary column 7, the injected gas escapes through this second end 7b left clear. The circulation of gas sustained in this capillary column 7 allows the thin sol layer 3 deposited on the internal wall of the capillary column 7 to dry.

Therefore it should be noted that the gas allows the displacement of the plug inside and along the capillary column 7 as well as the drying of the thin sol layer deposited on the internal wall of the capillary column 7. This drying of the thin sol layer will moreover begin immediately after deposition of this thin layer on the internal wall of the capillary column 7.

Under the effect of this drying, the sol gels and the alcohol and then the water evaporate. Evaporation of the alcohol allows the surfactant to be organized in micelles, these micelles in turn being organized as a network, a so called pore-forming network, which is compact. The evaporation of the water, as for it, promotes the condensation of the gel around these micelles: the silanol groups of the gel not having formed any covalent bonds during gelling react with each other, on the one hand, for generating siloxane bridges which form the bases of the silica matrix and with OH groups of the internal wall of the capillary column 7, on the other hand, which reinforces at the end of the method according to the invention, the covalent anchoring of the stationary phase on this internal wall.

After drying, the surfactant is removed in order to release the mesopores and thus make available the whole surface of the mesoporous silica. This removal of the surfactant may for example be accomplished by calcination or by washing with a solvent. This solvent may be an alcohol, such as ethanol or isopropanol, or further a ketone, for example acetone.

The calcination may be accomplished under a gas flow, by means of a gas, in particular of an inert gas as those mentioned above (helium or nitrogen) and at a temperature comprised between 100° C. and 500° C., this temperature is of course to be adapted depending on the surfactant present in the sol. This gas should be dry and is advantageously introduced into the capillary column through the tube. It is also possible to use oxygen gas which has the advantage of lowering the temperature of this calcination step by about 100° C.

Making a Capillary Column According to the Method of the Invention

The method was applied on a capillary column in molten silica with a length of 1 m and an internal diameter of 100 µm.

Activation of the Internal Wall of the Column

A Brown's mixture made by dissolving 140 mg of NaOH in a mixture comprising 15 ml of water and 20 ml of ethanol, was introduced into the capillary column, with a pressure gradient of 1 bar for 30 minutes, i.e. at a flow rate of the order of 0.2 µl/s. The capillary column was then washed with distilled water with a 1 bar pressure gradient until a neutral pH is attained at the outlet of the capillary column. The capillary column was then dried by nitrogen flow, with a pressure gradient of 1 bar.

Preparation of the Sol

The sol produced is formed from tetraethylorthosilicate (TEOS), ethanol and water in TEOS/EtOH/$H_2O$ molar ratios of 1/3.8/5.

4.4 ml of ethanol and 4.4 ml of TEOS were added to 1.8 ml of a solution of water and hydrochloric acid with a pH=1.25. This first solution was refluxed at 60° C. for 60 min. 102 mg of hexadecyltrimethylammonium bromide (CTAB) were dissolved in 0.5 ml of ethanol, with ultrasound, by slightly heating (30° C.).

It was then proceeded with mixing, by means of a vortex, 1.5 ml of the first solution in the solution containing CTAB. The obtained final solution was filtered on a polytetrafluoroethylene (PTFE) membrane with a porosity of 0.2 µm.

This final solution has a TEOS/CTAB molar ratio of 1/0.1.

Deposition of the Sol into the Column

About 2 µl of the sol prepared in the previous step were introduced into the column with a pressure gradient of 1 bar, for 10 seconds. Next, the drying step was conducted by having nitrogen flow with a pressure gradient of 1 bar for 15 minutes at a temperature of 20° C. The temperature of the nitrogen was then raised at a rate of 1° C./minute, until a temperature of 120° C. is attained, a temperature at which the nitrogen flow was maintained for 7 hours.

Calcination and Removal of CTAB

Helium was then introduced into the column with a 0.4 bar gradient for 20 minutes at a temperature of 120° C., Next, the temperature of the helium was raised at a rate of 4° C./minute until a first temperature of 230° C. was attained, this first temperature being then maintained for 90 minutes, and then the temperature of the helium was raised at a rate of 1° C./minute until a second temperature of 250° C. was attained, this second temperature being then maintained for 60 minutes.

Separation of the n-Alkanes

The thereby obtained capillary column after the four steps detailed above was used for achieving separation of a mixture of C1-C5 n-alkanes.

Figure 2:
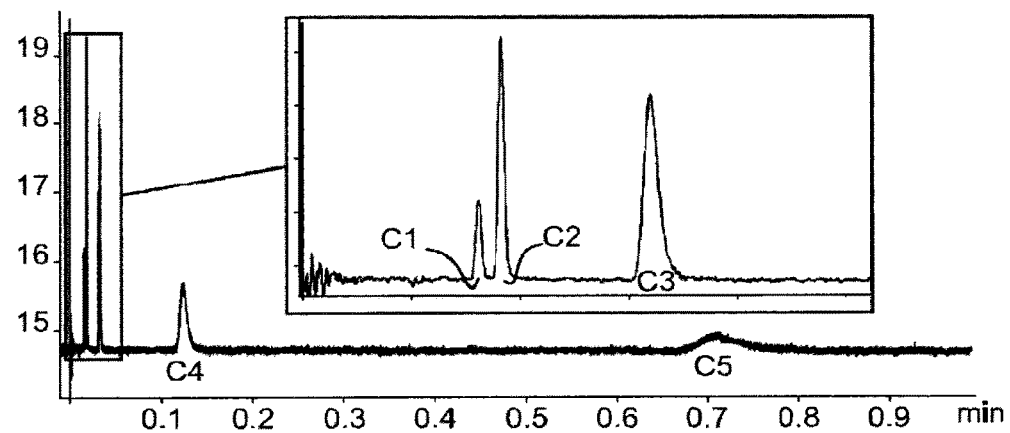
FIG. 2 is a chromatogram obtained with the application of a capillary column comprising a stationary phase in silica and manufactured according to the method of the invention.

The obtained chromatogram with this capillary column after injecting 0.5 µl of a mixture above (methane, ethane, propane, butane and pentane) is reproduced in FIG. 2. This chromatogram was obtained by connecting the thereby formed column to a commercial analysis device with reference Agilent GC6850 series 2, with a detector of the Flame Ionization Detector type. The injection conditions were the following: the temperature of the capillary column was 30° C., and the carrier gas used was helium under a pressure of 82.74 kPa (12 psi).

The chromatogram reproduced in FIG. 2 shows that all the compounds were well separated and this with very good separation efficiency, for example with 4,100 theoretical plates per meter for ethane.

Making a Microcolumn According to the Method of the Invention

The method was applied on a microcolumn in silicon with a length of 1.33 m and a rectangular section of 40 µm×160 µm.

Activation of the Internal Wall of the Column

A Brown's mixture made by dissolving 140 mg of NaOH in a mixture comprising 15 ml of water and 20 ml of ethanol, was introduced into the microcolumn, with a pressure gradient of 3 bars for 120 minutes, i.e. at a flow rate of the order of 0.3 µl/s. The microcolumn was then washed with distilled water with a 3 bar pressure gradient until a neutral pH is attained at the outlet of the microcolumn. The microcolumn was then dried by nitrogen flow, with a pressure gradient of 3 bars.

Preparation of the Sol

The sol produced is formed from tetraethylorthosilicate (TEOS), ethanol and water in TEOS/EtOH/$H_2O$ molar ratios of 1/3.8/5.

4.4 ml of ethanol and 4.4 ml of TEOS were added to 1.8 ml of a solution of water and hydrochloric acid with a pH=1.25. This first solution was refluxed at 60° C. for 60 min. 102 mg of hexadecyltrimethylammonium bromide (CTAB) were dissolved in 0.5 ml of ethanol, with ultrasound, by slightly heating (30° C.).

By means of a vortex, 1.5 ml of the first solution was mixed in the solution containing CTAB. The obtained final solution was filtered on a polytetrafluoroethylene (PTFE) membrane with a porosity of 0.2 µm.

This final solution has a TEOS/CTAB molar ratio of 1/0.1.

Deposition of the Sol into the Column

About 1.2 µl of the sol prepared in the previous step were introduced into the microcolumn with a pressure gradient of 4 bars, for 30 seconds. A drying step followed by having nitrogen flow with a pressure gradient of 4 bar for 20 minutes at a temperature of 20° C. The temperature of the nitrogen was then raised at a rate of 1° C./minute, until a temperature of 120° C. is attained, a temperature at which the nitrogen flow was maintained for 7 hours.

Calcination and Removal of CTAB

Helium was then introduced into the column with a 1.7 bar gradient for 20 minutes at a temperature of 120° C. Next, the temperature of the helium was raised at a rate of 4° C./minute until a first temperature of 230° C. was attained, this first temperature being then maintained for 120 minutes, and then the temperature of the helium was raised at a rate of 1° C./minute until a second temperature of 250° C. was attained, this second temperature being then maintained for 90 minutes.

Separation of the n-Alkanes

The thereby obtained microcolumn after the four steps detailed above was used for achieving separation of a mixture of $C_1$-$C_5$ n-alkanes.

Figure 3:
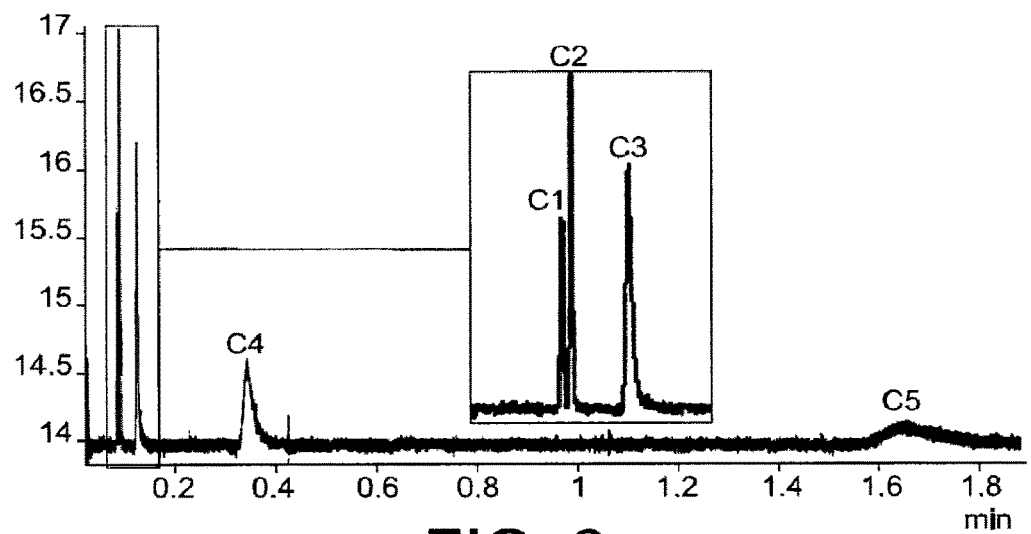
FIG. 3 is a chromatogram obtained with the application of a microcolumn comprising a stationary phase in silica and manufactured according to the method of the invention.

The obtained chromatogram with this microcolumn after injecting 500 ppm of a mixture above (methane, ethane, propane, butane and pentane) is reproduced in FIG. 3. This chromatogram was obtained by connecting the thereby formed column to a commercial analysis device with reference Agilent GC6850 series 2, with a detector of the Flame Ionization Detector type.

The injection conditions were the following: the temperature of the microcolumn was 30° C., the carrier gas used was helium under a pressure of 82.74 kPa (12 psi).

The chromatogram reproduced in FIG. 3 shows that all the compounds were well separated and this with very good separation efficiency, for example with 6,600 theoretical plates per meter for ethane.

BIBLIOGRAPHY

[1] J. Vial et al., *Journal of Chromatography A*, 1218, 2011, pages 3262-3266
[2] Rouqudrol et al., *Pure & Applied Chemistry*, 66(8), 1994, pages 1739-1758

The invention claimed is:

1. A method for manufacturing a chromatography column comprising a stationary phase made from a sol comprising a pore-forming agent, comprising:
    (a) introducing a sol comprising a pore-forming agent at a first end of the column,
    (b) moving said sol towards a second end of the column, so that a thin sol layer is formed on the internal wall of the column wherein said sol layer forms a gel on the internal wall of the column,
    (c) drying the gel, and
    (d) removing the pore-forming agent from the dried layer, so as to form a microporous, mesoporous layer or other porous layer, the size and/or the density of the pores being controlled, said porous layer forming the stationary phase.

2. The method according to claim 1, wherein the sol forms a plug, extending from the first end of the column and over a length of less than two-thirds of the total length of the column, the plug being moved along the column under the effect of a pressure.

3. The method according to claim 1, wherein (c) is carried out by circulating a gas inside the column and, if required, during (a).

4. The method according to claim 3, wherein the gas is air or helium, nitrogen or another inert gas.

5. The method according to claim 1, wherein the pore-forming agent comprises cetyltrimethylammonium bromide (CTAB), diblock copolymers of ethylene oxide and of propylene oxide, triblock copolymers of ethylene oxide and of propylene oxide, or another surfactant.

6. The method according to claim 1, wherein (d) is carried out after (c) with a treatment selected from the group consisting of calcination, washing with an organic solvent of the alcohol or acetone type, and UV insolation.

7. The method according to claim 6, wherein the calcination is carried out by circulating dry oxygen, dry helium, dry nitrogen or another dry gas inside the column, the temperature of this gas being comprised between 100° C. and 500° C.

8. The method according to claim 1, wherein (a) to (c) are reproduced at least once before applying (d).

9. The method according to claim 1, wherein further comprising subjecting the internal wall of the column to a preparation treatment prior to (a) to reinforce the adhesion of the sol on the internal wall, wherein said treatment increases the hydrophilicity of the internal wall.

10. The method according to claim 1, further comprising subjecting the internal wall of the column to an activation treatment prior to (a) to reinforce adhesion of the stationary phase, wherein the activation treatment promotes covalent grafting between the gel and the internal wall during the condensation of the gel.

11. The method according to claim 10, wherein the activation treatment of the internal wall of the column is carried out by oxidation of said internal wall, this oxidation being carried out by plasma, via a gas route or via a liquid route.

12. The method according to claim 1, wherein the internal wall of the column is in silicon, in silica, in molten silica, in polymer or in metal.

13. The method according to claim 1, wherein the stationary phase has a thickness of less than or equal to 3 μm.

14. The method according to claim 1, wherein the chromatography column is a capillary column with an internal diameter of less than or equal to 2 mm.

15. The method according to claim 1, wherein the chromatography column is a microcolumn for which at least one of the internal transverse lengths is less than or equal to 500 μm.

16. The method according to claim 1, wherein:
    the sol forms a plug, and
    (b) comprises moving the plug along the column.

17. The method according to claim 16, wherein moving the plug forms the thin layer of the sol on the internal wall of the column.

18. The method according to claim 16, comprising moving the plug under the effect of pressure.

19. The method according to claim 16, comprising forming the plug to have a length of 20 to 50 cm in the column.

20. The method according to claim 16, comprising selecting a moving speed of the plug to leave the thin layer of the sol having a desired thickness on the internal wall of the column.

21. The method according to claim 16, comprising selecting a solvent concentration of the sol to leave the thin layer of the sol having a desired thickness on the internal wall of the column.

22. The method according to claim 16, comprising selecting a volume of the sol to form the plug to leave the thin layer of the sol having a desired thickness on the internal wall of the column.

23. The method according to claim 16, comprising forming the plug to extend over a length less than two thirds of a length of the column.

24. The method according to claim 16, comprising forming the plug to extend over a length less than half of a length of the column.

25. The method according to claim 16, comprising forming the plug to extend over a length less than one third of a length of the column.

26. The method according to claim 16, comprising forming the plug to extend over a length less than one tenth of a length of the column.

27. The method according to claim 16, comprising forming the plug to extend from the first end over a length less than a length of the column.

28. The method according to claim 1, wherein:
    the sol forms a plug at the first end, and
    (b) comprises moving the plug from the first end to the second end.

29. The method according to claim 28, comprising moving the plug under the effect of pressure.

30. The method according to claim 1, comprising:
moving said sol towards a second end of the column to form the thin sol layer on the internal wall of the column and a passage from the first end to the second end.

31. The method according to claim 30, comprising:
flowing a gas through the passage to dry to sol layer.

32. The method according to claim 2, comprising moving the plug under the effect of pressure of a gas or of a supercritical fluid.

33. The method according to claim 32, wherein the gas is the same as a gas applied in (c).

* * * * *